(12) United States Patent
Stieghorst et al.

(10) Patent No.: US 10,792,854 B2
(45) Date of Patent: Oct. 6, 2020

(54) METHOD FOR MANUFACTURING A COMPONENT BY A GENERATIVE MANUFACTURING PROCESS, APPARATUS FOR MANUFACTURING A COMPONENT BY A GENERATIVE MANUFACTURING PROCESS, AND MEDICAL IMPLANT GENERATED FOR AN INDIVIDUAL PATIENT

(71) Applicant: MEDIZINISCHE HOCHSCHULE HANNOVER, Hannover (DE)

(72) Inventors: Jan Stieghorst, Nienhagen (DE); Theodor Doll, Bochum (DE)

(73) Assignee: MEDIZINISCHE HOCHSCHULE HANNOVER, Hannover (DE)

( * ) Notice: Subject to any disclaimer, the term of this patent is extended or adjusted under 35 U.S.C. 154(b) by 679 days.

(21) Appl. No.: 15/327,682

(22) PCT Filed: Jul. 17, 2015

(86) PCT No.: PCT/EP2015/066441
§ 371 (c)(1),
(2) Date: Jan. 20, 2017

(87) PCT Pub. No.: WO2016/012370
PCT Pub. Date: Jan. 28, 2016

(65) Prior Publication Data
US 2017/0203509 A1    Jul. 20, 2017

(30) Foreign Application Priority Data

Jul. 22, 2014 (DE) .................. 10 2014 010 677
Feb. 9, 2015 (DE) .................. 10 2015 101 810

(51) Int. Cl.
B29C 67/00 (2017.01)
B33Y 30/00 (2015.01)
(Continued)

(52) U.S. Cl.
CPC .......... *B29C 64/112* (2017.08); *A61B 5/0478* (2013.01); *A61N 1/05* (2013.01);
(Continued)

(58) Field of Classification Search
CPC ...... A61N 1/0541; A61N 1/0529; A61N 1/05; B29C 64/386; B29C 64/135;
(Continued)

(56) References Cited

U.S. PATENT DOCUMENTS 6,658,314 B1   12/2003   Gothait
7,120,486 B2   10/2006   Leuthardt
(Continued)

OTHER PUBLICATIONS

O'Doherty et al., "A brain-machine interface instructed by direct intracortical microslimulalion", Frontiers In Integrative Neuroscience, Sep. 2009, vol. 3, art. 20.
(Continued)

*Primary Examiner* — Robert J Grun
(74) *Attorney, Agent, or Firm* — W&C IP (57) ABSTRACT

The invention relates to a method for manufacturing a component (10) by a generative manufacturing process, wherein the component is entirely or partially produced from a liquid raw material (12), characterised in that the component is entirely or partially produced from a liquid raw material (12) that can solidify when heated, the raw material is discharged in liquid form into a manufacturing zone (1) and heated and hence solidified by a computer-controlled, targeted light spot, in that the point of incidence of a light beam (8) from a light beam source is continuously and/or gradually modified relative to the manufacturing zone (1).

10 Claims, 6 Drawing Sheets

(51) Int. Cl.

| | | |
|---|---|---|
| *A61N 1/05* | (2006.01) | |
| *B33Y 80/00* | (2015.01) | |
| *A61B 5/0478* | (2006.01) | |
| *B33Y 10/00* | (2015.01) | |
| *B33Y 50/02* | (2015.01) | |
| *B29C 64/112* | (2017.01) | |
| *B29C 64/135* | (2017.01) | |
| *B29K 105/00* | (2006.01) | |
| *B29L 31/00* | (2006.01) | |

(52) U.S. Cl.
CPC ......... *A61N 1/0529* (2013.01); *A61N 1/0541* (2013.01); *B29C 64/135* (2017.08); *B33Y 10/00* (2014.12); *B33Y 30/00* (2014.12); *B33Y 50/02* (2014.12); *B33Y 80/00* (2014.12); *A61B 2562/125* (2013.01); *B29K 2105/0058* (2013.01); *B29L 2031/753* (2013.01)

(58) Field of Classification Search
CPC .............. B29C 64/112; A61B 5/0478; A61B 2562/125; B33Y 80/00; B33Y 50/02; B33Y 30/00; B33Y 10/00; B29L 2031/753; B29K 2105/0058
See application file for complete search history.

(56) References Cited

U.S. PATENT DOCUMENTS

| | | |
|---|---|---|
| 2005/0288813 A1 | 12/2005 | Yang et al. |
| 2009/0014916 A1 | 1/2009 | Nagai |
| 2010/0208006 A1 | 8/2010 | Selinfreund |
| 2015/0250934 A1 | 9/2015 | Min |

OTHER PUBLICATIONS

Sinai et al., "Electrocorticographic high gamma activity versus electrical cortical stimulation mapping of naming", Brain, 2005, pp. 1556-1570, vol. 128.

Formaggio et al., "Frequency and time-frequency analysis of intraoperative ECoG during awake brain stimulation", Frontiers In Neuroengineering, Feb. 2013, vol. 6, art. 1.

Lantada; Morgado, Rapid Prototyping for Biomedical Engineering: Current Capabilities and Challenges, Annu Rev Biomed Eng, 2012, pp. 73-96, vol. 14.

Breuninger et al., "Generative Fertigung mil Kunststoffen", 2013, pp. 27-78, Springer Verlag Berlin Heidelberg.

"Cortac Epilepsy Electrods", PMT Corporation, Web, http://www.pmtcorp.com/cortac.html.

"Subdural Electroded", ADTECH, Web, http://adtechmedical.com/subdural-electrodes.

METHOD FOR MANUFACTURING A COMPONENT BY A GENERATIVE MANUFACTURING PROCESS, APPARATUS FOR MANUFACTURING A COMPONENT BY A GENERATIVE MANUFACTURING PROCESS, AND MEDICAL IMPLANT GENERATED FOR AN INDIVIDUAL PATIENT

The invention relates to a method for producing a component by means of an additive manufacturing process. The invention further relates to an apparatus for producing a component by means of an additive manufacturing process and to a medical implant generated for an individual patient. In particular, the invention relates to the field of additive manufacturing of components from liquid raw material solidifiable by heating, for example for medical implant treatment using personalized implants.

Examples of additive manufacturing processes are stereolithography, selective laser melting, selective laser sintering, fused deposition modeling, laminated object modeling, 3D printing and gas dynamic cold spray, especially also all manufacturing methods of rapid prototyping, of rapid tooling and of rapid manufacturing.

Polyjet modeling, digital light processing and stereolithography are known in the field of additive manufacturing from liquid plastics, with stereolithography currently being the most accurate of all additive manufacturing methods (J. Breuninger, R. Becker, A. Wolf, S. Rommel and A. Verl, Generative Fertigung mit Kunststoffen [Additive manufacturing with plastics], Springer-Verlag Berlin Heidelberg, 27-28 (2013)). The basis of these methods is the layer-by-layer application and the layer-by-layer structuring cross-linking of a photosensitive polymer, which is crosslinked by UV radiation. These methods are used especially in prototype construction, with initial methods for serial production being in the course of implementation. In the area of medical implant treatment, additive methods are subsumed under the term "medical rapid prototyping". The methods are used for manufacturing dimensional models of human anatomical structures, which are created on the basis of medical imaging. Currently, medical rapid prototyping methods are used, inter alia, in the treatment of hard-tissue defects, such as, for example, cranial defects, in which it is possible, with the aid of electron beam melting or laser sintering methods, to produce directly matched metal cranial plates (A. D. Lantada and P. L. Morgado, Annu. Rev. Biomed. Eng. 14, 73-96 (2012)). By contrast, in the area of soft-tissue implants, direct additive production of medical implants is not possible, since, currently, the polymers used here can only be molded from molds and cannot be directly printed.

It is therefore an object of the invention to specify a method and an apparatus for producing a component by means of an additive manufacturing process in which an initially liquid raw material can be used as the material to be processed. Furthermore, it is intended that a medical implant be specified which can be manufactured from such a material by means of an additive manufacturing process.

This object is achieved as claimed in claim 1 by a method for producing a component by means of an additive manufacturing process, wherein the component is entirely or partly produced from a liquid raw material solidifiable by heating, wherein the raw material is dispensed in liquid form into a manufacturing zone and is, as a result of computer-controlled, punctual targeted light irradiation, heated and thereby solidified, by the impact point of a light beam of a light-beam source relative to the manufacturing zone being altered in a continuous and/or in a step-by-step manner.

The invention solves a substantial problem which occurs in the use of a liquid raw material without the aid of a negative mold, namely that the raw material flows away or flows apart relatively rapidly from the application point. The invention solves this by computer-controlled, punctual targeted light irradiation and also by the fact that the raw material used is a raw material solidifiable by heating. As a result, the raw material applied in liquid form can be cured in a targeted manner relatively rapidly at least to the extent that it maintains its shape and no longer flows away.

A further advantage is that it is possible to use raw materials which cannot be cured by ultraviolet light irradiation, i.e., which do not comprise UV crosslinkers. As a result, it is possible in many applications to produce better tolerable components, especially medical implants. As raw material, it is possible to use, in particular, medical materials which are already authorized.

The problem mentioned at the start in the use of liquid raw material is significant in the production of flexible implants, since a manufacture of individually matched polymer-based implants did not appear possible until now. It is desired that, for an optimal effect, solid and also flexible implants should be matched to and positioned at the individual target site of each individual patient as specifically as possible. If this is not the case, the implant can, in the worst case, not only fail to fulfill its intended function, but also damage healthy structures and processes. A pacemaker electrode, an electrode shaft of a cochlear implant, a probe for deep brain stimulation or an implant for cortical discharge would be of little use if their electrode contacts were not to be positioned in the immediate surroundings of the targeted cells. Thus, a method which, in addition to the production of anatomically matched implants from solid materials, also allows the production from flexible materials would be ideal. Furthermore, materials which are already available should be able to be processed, since only photosensitive plastics can be processed using the aforementioned methods. In medical technology, this strongly limits especially the choice of material, since plastics which are photosensitive and simultaneously biocompatible are rare. When using UV crosslinkers, common materials such as, for example, silicone elastomers (application in breast implants, cochlear implant systems, probes, pacemakers, etc.) can only be used in short-term applications, since the UV crosslinkers are not authorized for long-term applications. By contrast, silicone elastomers which crosslink due to heat have been tested and are already authorized for long-term application.

As already mentioned, the impact point of the light beam of the light-beam source relative to the manufacturing zone is altered in a continuous and/or in a step-by-step manner. For example, this can be achieved by the light-beam source being controllable with respect to the beam direction of the light, and so the beam direction of the light beam is altered in a continuous and/or in a step-by-step manner and different sites of the manufacturing zone are thus irradiated. Alternatively or in combination therewith, it is also possible for the manufacturing zone to be alterable in position, for example in the form of a table which is movable in at least two directions in space and on which the component to be additively manufactured is constructed.

The manufacturing zone can be in particular a manufacturing zone of an apparatus for producing a component by means of an additive manufacturing process, for example a planar or curved surface on which the raw material is dispensed and where the component then arises additively.

According to an advantageous development of the invention, the solidified raw material further has a high elasticity. This has the advantage that it is possible with the invention to produce flexible or highly elastic components, such as, for example, soft-tissue implants for the medical area. The solidified raw material can be in particular a rubbery-elastic material. According to an advantageous development of the invention, the solidified raw material has a Shore hardness within the range from 10 to 90 Shore A, more particularly 20 to 60 Shore A.

The raw material can be in particular a polymer material. In this case, the raw material in the liquid state is also referred to as prepolymer. In particular, the raw material can be a silicone material, for example silicone rubber. Biocompatible silicones authorized for the medical area are in particular obligatory for the production of medical implants.

According to an advantageous development of the invention, the light beam of the light-beam source is formed as a finely focused light beam. In particular, the light beam can have a diameter ≤300 μm, even better ≤200 μm, at the impact point on the raw material to be solidified. This allows the production of the component with a high three-dimensional resolution, and so it is also possible to produce finely detailed components.

According to an advantageous development of the invention, the impact point of the light beam of the light-beam source relative to the manufacturing zone is, during the manufacturing process for the component, repositioned in relation to a raw material dispensing unit which dispenses the raw material in a dropwise manner, and so raw material drops freshly dispensed by the raw material dispensing unit are immediately heated and thereby solidified by the light beam. This has the advantage that the component can be produced especially quickly virtually in any desired design by point-by-point application of the raw material. Owing to the heat generated for a short time by the light beam after dispensing of a raw material drop, said drop is immediately solidified to the extent that it cannot flow away. The repositioning of the impact point of the light beam with the raw material dispensing unit can, for example, be realized such that the light-beam source is mechanically coupled in a fixed manner with the raw material dispensing unit and that the beam direction of the light beam is aligned accordingly, and so the light beam automatically strikes a raw material drop freshly dispensed by the raw material dispensing unit. It is also possible for the light-beam source and the raw material dispensing unit to be mechanically decoupled from one another. In this case, it is advantageous to reposition the beam direction of the light beam of the light-beam source in relation to the raw material dispensing unit in a computer-controlled manner.

According to an advantageous development of the invention, the liquid raw material in the raw material dispensing unit is already preheated before dispensing and thus partially solidified by means of a preheating unit. This has the advantage that the viscosity of the liquid raw material can be somewhat increased in advance (prevulcanization) and thus the energy input to be generated by the light beam after dispensing of the raw material from the raw material dispensing unit is reduced. As a result, it is possible to increase the working speed and precision of the additive manufacturing process.

According to an advantageous development of the invention, the raw material is mixed with a curing-promoting material. For example, this can be done in advance, i.e., before the raw material is used in the additive manufacturing process, for example by the manufacturer, or during the additive manufacturing process. For example, the mixing with the curing-promoting material can be done within the raw material dispensing unit via a mixer arranged therein. The admixing of a curing-promoting material has the advantage that the energy input to be generated by the light-beam source in order to solidify the liquid raw material is reduced. This is likewise advantageous for a high working speed and precision of the additive manufacturing process.

According to an advantageous development of the invention, light-absorbing particles are admixed as curing-promoting material, which particles increase the light absorption of the thus formed mass and thus quicken the solidification due to light irradiation.

According to an advantageous development of the invention, the light beam is an infrared light beam or has at least predominantly infrared spectral components. This has the advantage that a high heating efficiency in the raw material to be solidified can be achieved by means of the light-beam source. For example, the light-beam source can be a laser light source, for example an infrared laser diode, a carbon monoxide laser or a CO2 laser. A ceramic infrared emitter is further suitable. The desired, finely focused light beam of the light-beam source can also be generated via a suitable optics system, for example a lens system.

According to an advantageous development of the invention, the component is produced with multiple functional layers, by particular layers being applied by the application of a further raw material to already solidified regions of the component, which layers are in turn solidified by computer-controlled targeted light irradiation. As already explained above, the application of the further layers can likewise be effected in a point-by-point manner.

According to an advantageous development of the invention, the component is produced from multiple different materials, with at least one holding structure for at least one further subelement of the component being generated from the raw material solidified by light irradiation. In this way, it is also possible to generate complex technical components, especially also components having electrically conductive structures. In this way, it is possible to generate, for example, subdural electrode arrays by means of the invention. In this case, the further materials used, which are used besides the liquid raw material, need not necessarily be generated concomitantly in the same additive manufacturing process as the actual component; instead, they can also be provided as prefabricated parts, for example in the form of metal lattice arrays.

According to an advantageous development of the invention, the raw material is not completely solidified by means of the computer-controlled, punctual targeted light irradiation in a first pass. This has the advantage that the manufacturing process can be further quickened. The residence time of the light beam at a particular raw material point can be reduced as a result. A further advantage is that the raw material can, as a result of its incomplete solidification, have properties which are favorable for the adhesion of a further applied layer of the raw material.

After carrying out the stated first pass, it is possible to effect a further or final solidification of the raw material in a second pass. For example, this can be effected by general heating of the otherwise already completely manufactured component, for example in an oven, or by renewed punctual light irradiation, with again the impact point of the light beam relative to the manufacturing zone or to the component already now present being altered. In the second pass, the light beam can be less finely focused, i.e., have a larger diameter in the impact point than in the first pass.

According to an advantageous development of the invention, the component is subjected to a heat after-treatment after complete or partial conclusion of the solidification process for the liquid raw material in the second pass by computer-controlled, targeted light irradiation.

The manufacturing zone can have in particular a platform on which the component is generated. For instance, the component can be produced by computer-controlled point-by-point application of the liquid raw material to the platform and/or to already solidified raw material and subsequent solidification due to light irradiation of a particular raw material point which is still liquid.

According to an advantageous development of the invention, one or more liquid raw material points are applied to the platform and/or to already solidified raw material and are solidified by light irradiation before further points of liquid raw material are applied. This also counteracts flowing away of the liquid raw material, by it being quickly heated and thus solidified in a point-by-point manner.

According to an advantageous development of the invention, the liquid raw material is applied in a layer-by-layer manner to a platform and/or to already solidified raw material and is solidified by computer-controlled, targeted light irradiation before a further layer of liquid raw material is applied. In contrast to the point-by-point application of the raw material, the layer-by-layer application has the advantage that the working speed of the manufacturing process can be further increased. Excess raw material not solidified by the light beam can then be later removed.

According to an advantageous development of the invention, the platform is lowered each time after the application of one or more layers of the raw material. In this way, the raw material dispensing unit need not be designed to be movable in all three directions in space; instead, it can, for example, be movable only in one plane, i.e., in two directions in space. This simplifies the mechanics of an apparatus for producing the component.

According to an advantageous development of the invention, the liquid raw material is solidified by multiple light beams which intersect in one point of the raw material, which point is to be solidified. This has the advantage that other regions of the raw material that are already solidified are not undesirably heated. Moreover, this can also increase the working speed of the additive manufacturing process. The intersecting light beams can, for example, be emitted by two separately computer-controlled light-beam sources.

According to an advantageous development of the invention, in one or more regions of the component to be produced, electrically conductive material is admixed with the raw material in the liquid state. In this way, it is possible to form certain regions of the produced component as electrically conductive regions. The electrically conductive material is held at a defined position in the produced component by the raw material in the solidified state. As electrically conductive material, it is possible, for example, to use carbon nanotubes. The mixing with the electrically conductive material can be done within the raw material dispensing unit via a mixer arranged therein.

According to an advantageous development of the invention, the emission of light from the light-beam source to the raw material is switched on and off by means of a shutter. This has the advantage that it is also possible to use those light-beam sources where the switch-on and switch-off process is tainted by relatively huge dead times, such as, for example, electrically heated spiral-wound filaments. When using laser diodes as light-beam source, such a shutter will not be necessary in many cases, but can nevertheless also be used advantageously in such cases.

According to an advantageous development of the invention, the component is, as a result of controlling the targeted light irradiation, produced with elasticity values of the solidified material that differ from region to region. This has the advantage that one component can be produced from the same raw material, which ultimately has a desired inhomogeneous elasticity distribution. Here, the material-specific elasticity can in particular vary in different regions of the component.

The object stated at the start is further achieved by an apparatus for producing a component by means of an additive manufacturing process, comprising:
a) a manufacturing zone at which the component to be produced is formed by means of raw material which is to be arranged there, which is liquid and which is solidifiable by heating,
b) a raw material dispensing unit for dispensing the raw material to the manufacturing zone,
c) a light-beam source for emitting a light beam,
d) a controllable actuator mechanism which makes it possible to alter the impact point of the light beam of the light-beam source relative to the manufacturing zone in a continuous and/or in a step-by-step manner,
e) a control unit with a computer, which control unit is configured to control the actuator mechanism,
f) wherein the apparatus is configured to carry out a method for producing a component by means of an additive manufacturing process of the type explained above.

Using such an apparatus, it is likewise possible to realize the advantages stated above with regard to the method. The above-explained equipment-based developments of the invention, too, are also realizable as advantageous developments of the apparatus. In particular, the apparatus can comprise a shutter. The shutter can be controllable by means of the control unit. Furthermore, the apparatus can comprise multiple light-beam sources which are controllable with respect to the beam direction. The light-beam sources can, with respect to their beam direction and/or with respect to the emission of light (brightness or switching on/switching off of the emission of light), be controllable by the control unit. The light-beam source can be an infrared light-beam source or have at least predominantly infrared spectral components in the emitted light. In particular, the light-beam source can be designed as a laser light source.

The object stated at the start is further achieved by a medical implant generated for an individual patient, composed of rubbery-elastic material without a stabilizing scaffolding structure, having one or more electrodes which are embedded in the rubbery-elastic material and which, at least at a particular external contact surface, are not covered by the rubbery-elastic material. Such a medical implant can be produced additively, for example using a method by means of an additive manufacturing process of the type explained above and/or using an apparatus of the type explained above. In this way, medical implants for individual patients can be provided efficiently, precisely and rapidly. The medical implant has a pixel structure owing to the additive production. However, this is practically imperceptible, at least not disturbing, in the case of an appropriately high resolution of the additive manufacturing process, i.e., when using a finely focused light beam and accordingly small impact points of the light beam on the raw material to be solidified. The rubbery-elastic material of the medical implant can have a Shore hardness within the range from 10 to 90 Shore A, more particularly 20 to 60 Shore A. The implant can be formed in a multilayer manner with multiple functional layers.

According to an advantageous development of the invention, the implant is designed as an ECoG electrode array, as a pacemaker electrode array, as a cochlear implant electrode array or as a brainstem implant electrode array.

According to an advantageous development of the invention, one, more or all electrodes of the implant are formed by electrically conductive material admixed loosely with the rubbery-elastic material of the implant. As electrically conductive material, it is possible to use the carbon nanotubes already mentioned. In this way, the final implant with the electrodes continues to maintain its overall highly elastic properties.

According to an advantageous development of the invention, the implant has specific elasticity values of the rubbery-elastic material that differ from region to region. In this way, the implant can, depending on the application, also be adjusted with respect to its elastic properties, for example having external, more elastic regions and a central region with a lower specific elasticity.

The invention provides further advantages. Just through the possibility of being able to use established and authorized plastics, it is possible to realize the production of new products which, especially in medical technology, can be produced with distinctly reduced development and authorization costs. Furthermore, the proposed invention allows the manufacture of personalized implants which promise a distinctly improved match to the anatomy of the patient. This entails distinct advantages which are to be shown in the following application examples. Besides the stated system-related advantages, the crosslinking by means of IR radiation has the method advantage that the irradiated volume is crosslinked in a location-independent manner and is thus not bound to heat conduction and convection through the surface. This allows, firstly, a more rapid crosslinking, a potentially higher crosslinking temperature and, associated therewith, a quickened rise in viscosity that significantly increases the shape accuracy of the component.

The following embodiments of the invention are also advantageous:

1. A method for producing a printed component, characterized in that the component body is produced from a polymer which crosslinks due to heat and which is crosslinked by means of targeted infrared irradiation.
2. A base body produced in accordance with The method as claimed in embodiment 1, characterized in that multiple functional layers are generated by the application of further polymers which crosslink due to heat and which are crosslinked by targeted infrared irradiation.
3. A base body produced in accordance with The method as claimed in embodiment 1, characterized in that the polymer which crosslinks due to heat is crosslinked by irradiation with an infrared laser, carbon monoxide laser, a CO2 laser, infrared diode and a ceramic infrared emitter.
4. A base body produced in accordance with The method as claimed in embodiment 1 or 2, characterized in that the base body is produced by point-by-point application of the prepolymer to a planar platform and subsequent crosslinking, in line with embodiment 3.
5. A base body produced in accordance with The method as claimed in embodiment 1 or 2, characterized in that the base body is produced by point-by-point application of the prepolymer to a structured platform and subsequent crosslinking, in line with embodiment 3.
6. A base body produced in accordance with The method as claimed in embodiment 1 or 2, characterized in that the base body is produced by layer-by-layer application of the prepolymer to a straight lowerable platform and subsequent crosslinking, in line with embodiment 3.
7. A base body produced in accordance with The method as claimed in embodiment 1 or 2, characterized in that the base body is produced by layer-by-layer application of silicone rubber prepolymer and subsequent crosslinking, in line with embodiment 3.

The invention will be more particularly elucidated below on the basis of exemplary embodiments with use of drawings, showing FIG. 1—3D printing method for multicomponent components with layer-by-layer polymer application (left, FIG. 1a)) and point-by-point polymer application (right, FIG. 1b)). The system for layer-by-layer polymer application comprises: a lowerable platform 15, the solidified component 10, the infrared laser 3, multiple wipers 17 for applying the prepolymers. The uncrosslinked prepolymer 12 must be removed at the end of the process. The system for point-by-point polymer application comprises: a fixed platform 15, the vulcanized component 10, the infrared laser 3 and printheads/dispensers 2 for applying the prepolymers.

In the figures, the same reference signs are used for elements which correspond to one another.

Figure 1:
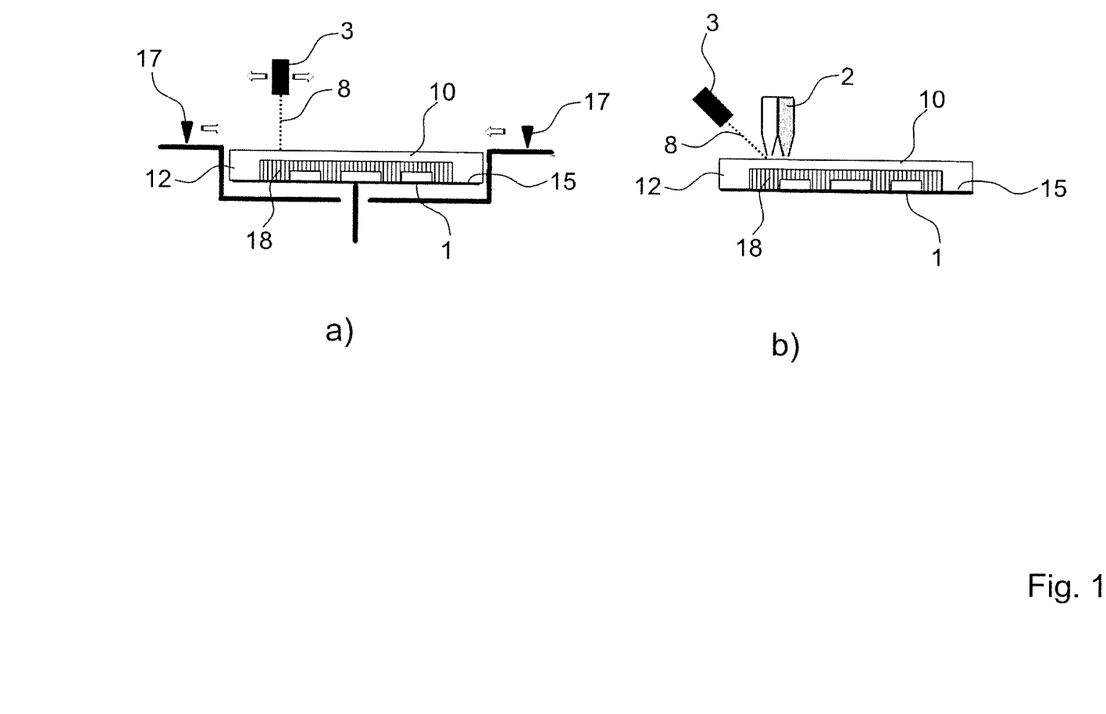

Besides the elements already mentioned, FIG. 1a) shows that the component 10 is produced as a medical implant with embedded electrodes. Within the rubbery-elastic material of the component 10, a metal structure 18 is present for forming the electrodes. Owing to the light beam 8 emitted by the light-beam source 3, there is a solidification of the prepolymer which is still liquid. The platform 15 is situated in a manufacturing zone 1 of an apparatus for producing the component 10.

In FIG. 1b), the abovementioned dispensers 2 form a raw material dispensing unit for the dropwise dispensing of the liquid raw material.

Figure 2:
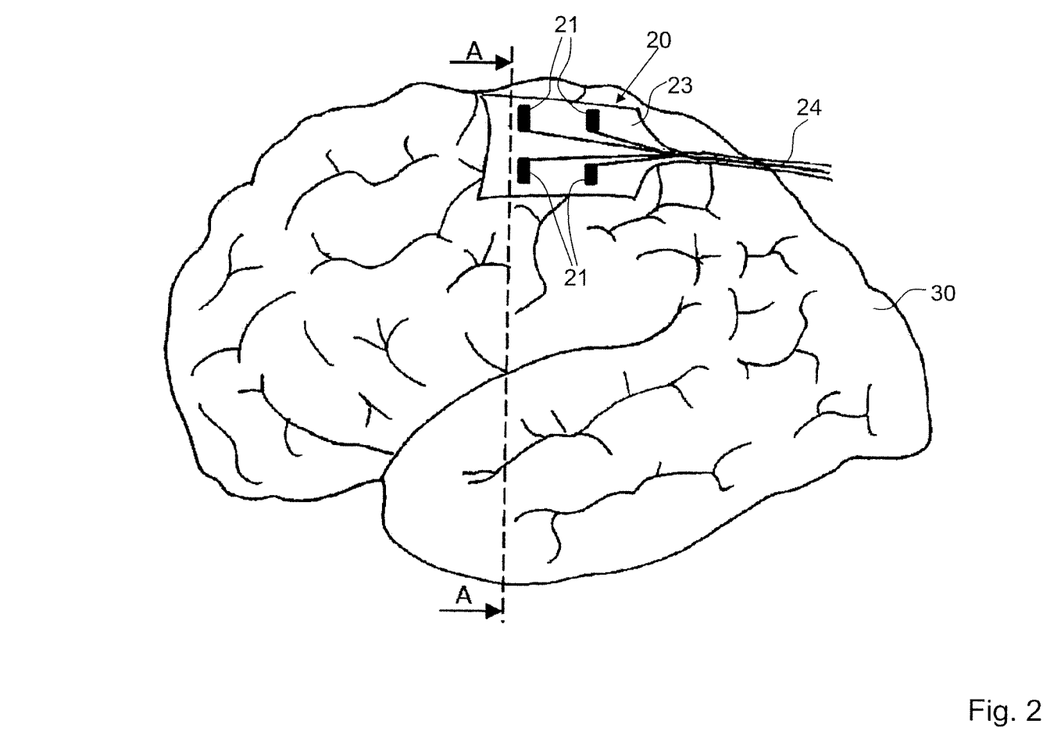
FIG. 2—Cortex surface 30 with an individually matched 4-contact grid electrode array 20. The drawn-in sectional view A-A is depicted in FIG. 3.

FIG. 2 shows a medical implant 20 generated for an individual patient and applied to a brain surface 30, in the form of an electrode array in which there are electrodes 21 which are embedded in rubbery-elastic material and which are electrically contactable via electrical connecting lines 24. The implant does not have a stabilizing scaffolding structure and can thereby be matched especially flexibly to the brain surface. The electrodes and also the connecting lines 24 can be formed from the abovementioned metal structure 18.

As mentioned, it is advantageous that already established materials can be used for the direct additive manufacture of individual structures. Especially in medical technology, this will distinctly reduce the development and authorization costs, since no new materials need to be developed and authorized. We therefore propose the production of flexible structures/implants from already established plastics which crosslink due to heat and which, in the liquid state, are crosslinked in a shape-faithful manner by the action of an infrared radiation spectrally matched to the specific absorption behavior of the plastic. The basis thereof is the proven selective absorption behavior of common plastics, such as, for example, polydimethylsiloxane or polyvinyl chloride in the long-wave IR range, which can, inter alfa, be generated by means of IR diodes, ceramic emitters and various laser systems. For the targeted crosslinking of fine structures, laser systems (acting in a point-by-point manner) are advantageous in particular, since IR diodes are currently not efficient enough and ceramic emitters are, owing to their diffuse radiation, complicated to focus. Thus, in a 3D printing method, the prepolymer can be applied to a platform with layer-by-layer or point-by-point polymer application and be crosslinked in a point-by-point manner using a movable infrared laser; see FIG. 1. Similarly to stereolithography, the layer-by-layer polymer application (FIG. 1a), left) is done via various wipers 17 on a lowerable platform 15. In the case of the point-by-point polymer application (FIG. 2, right), movable extruder or dispenser devices 2 are advantageous, which devices allow an exact dispensing of the applied prepolymer to the platform 15. Unaffected thereby, an area-by-area crosslinking can be carried out in both cases, it being necessary to fundamentally note that the shape accuracy depends on any absorbed temporal surface energy and the rheological crosslinking behavior of the plastic.

Within the scope of a further design of the invention, it is possible to evaluate the manufacturability of composite materials and of multicomponent components. In this regard, the use of multi-extruders or piezo-based or ultrasound-based printheads is advantageous. In addition, it is conceivable to add IR-absorbing particles which, when introduced into the prepolymer, increase the absorbed beam power.

Exemplary Embodiment 1: Use of the Proposed Invention as a Strip Electrode or Grid Electrode for Subdural Discharge and Stimulation With respect to the prosthetic treatment of motor-impaired patients, and also for the diagnosis and therapy of diseases of the cerebral cortex, it is conceivable to use long-term stable subdural electrodes which can discharge (electrocorticogram) and stimulate (subdural microstimulation) (J. E. O'Doherty, M. A. Lebedey, T. L. Hanson, N. A. Fitzsimmons and M. A. L. Nicolelis, Frontiers in Integrative Neuroscience 3, 1-(2009), U.S. Pat. No. 7,120,486 B2). As a result, it is possible to create a bidirectional interface for recording movement intentions and for applying a somatosensory feedback, which interface can be used for the intuitive control of prostheses and orthoses. An ideal of said subdural electrodes are so-called electrocortical grid arrays (ECoGs), which have already been used clinically for 20 years for presurgical diagnostics for epilepsy patients. ECoGs are silicone-based lamellar neural implants which are directly positioned on the surface of the brain. Owing to a multiplicity of electrodes embedded in the silicone, usually composed of platinum materials or stainless steels, it is possible to measure electrical activities of the cerebral cortex and to transmit them via connecting lines (pigtail harnesses, cable harnesses) to a measurement computer. The available systems are not suitable for a prosthetic and therapeutic treatment, since they do not stimulate, do not provide fine resolution, and cannot match the individual anatomical structures of the patient. Thus, ECoGs are typically manufactured in fixed dimensions which fit "average patients", but do not take into account the individual topography of the brain of each patient. They have between 4 and 64 electrode contacts, a contact diameter of 2 mm, 3 mm or 4.5 mm and a thickness of about 1.5 mm (A. Sinal, C. W. Bowers, C-M. Crainiceanu, D. Boatman, B. Gardon, R. P. Lesser, F. A. Lenz and N. E. Grone, Brain 128, 1556-1570 (2005); Cortac® Epilepsy Electrodes, PMT Corporation, Chanhassen, USA; Adtech, Racine, USA). This is significant, since the attachment of electrodes to nerve structures strongly depends on the "perfect fit" of the electrode layer. For example, Formaggio et al. (2013), in their study concerning discharge by means of ECoG with simultaneous stimulation of the primary motor cortex and of the primary sensory cortex, find that the attained discharge areas and the positions of the electrode contacts of the conventional ECoG used distinctly differ among the patients examined because of the individual position of the motor cortex (E. Formaggio, S. F. Storti, V. Tramontano, A. Casarin, A. Bertoldo, A. Flaschi, A. Talacchi, F. Sala, G. M. Toffolo and P. Mananotti, Frontiers in Human Neuroscience 6, 1-8 (2013)). On this basis, an adequate treatment of all patients is not achieved with standard implants.

Figure 3:
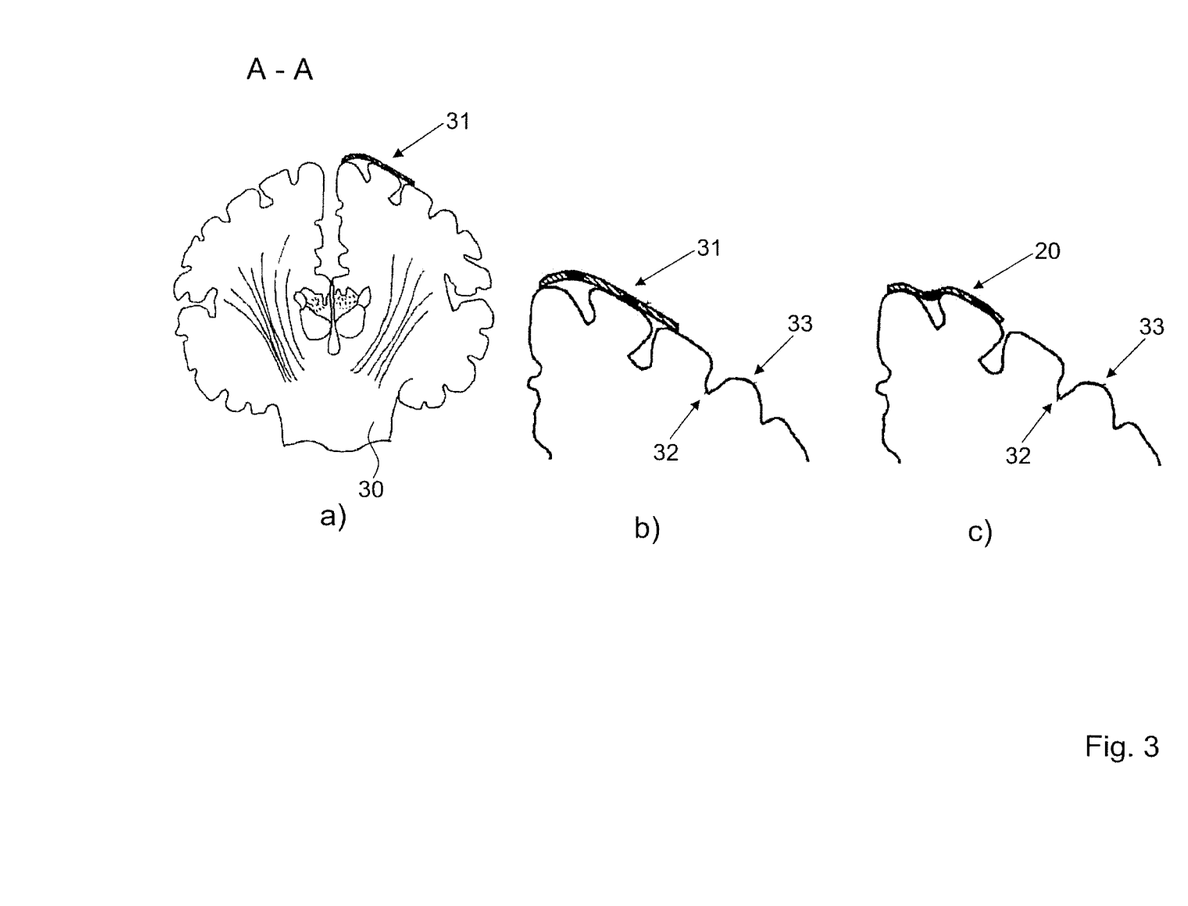
FIG. 3—Sectional view A-A of the brain 30 with a conventional (rigid) 4-contact grid electrode array 31 (left, FIG. 3a) and enlarged view at the center (FIG. 3b) and a personalized flexible 4-contact grid electrode array 20 (right, FIG. 3c)). The rigid grid electrode array 31 does not match the sulci 32 and gyri 33 of the cortex surface. The personalized grid electrode array 20 allows a better match to the cortex topography.
Figure 4:
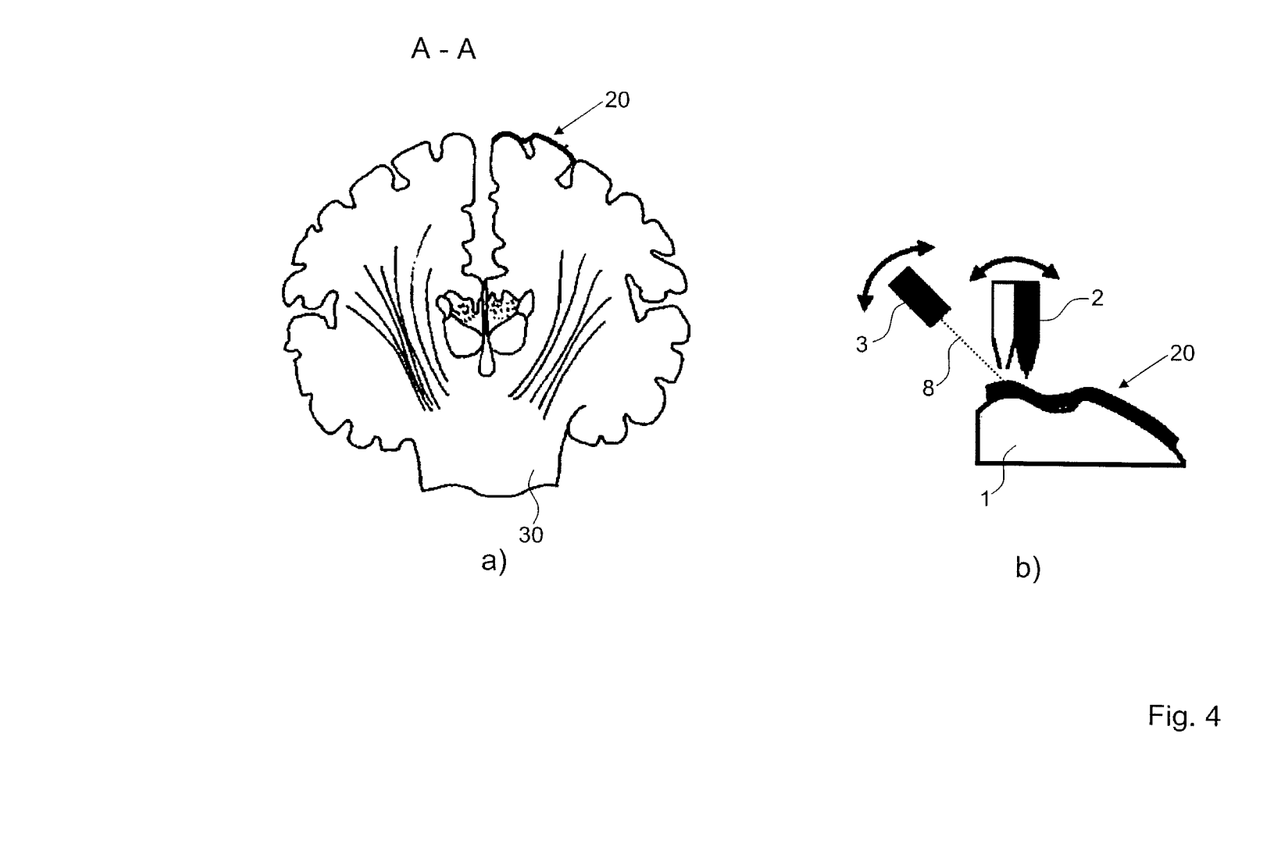
FIG. 4—Sectional view A-A (left, FIG. 4a)) of the brain 30 with intended implant position for the personalized grid electrode array 20 and 3D printing method (right, FIG. 4b)) with individually manufactured printing underlay 1, printed implant 20, movable infrared laser 3 and movable printheads/dispensers 2 for applying the prepolymers to the printing underlay.

With the proposed invention, it is possible to manufacture previously unavailable patient-personalized subdural electrode systems which can be utilized for diagnostics, therapeutics and prosthetics; see FIG. 2 and FIG. 3. To this end, it would be possible, on the basis of 3D volume data sets of the patient with use of computer-aided manufacturing techniques (CAM techniques), to model and develop grid electrode arrays which are matched to the anatomy of the patient. It would subsequently be possible to manufacture these in a 3D printer modified for silicone printing. To this end, firstly, the implant base body composed of a biocompatible silicone rubber which crosslinks on the basis of temperature is sprayed onto a printing bed using a movable dispenser and simultaneously vulcanized within a few seconds using a movable infrared laser beam. Experiments have shown that a vulcanization of a 2 mm thick silicone sample can be carried out in less than 45 seconds. This time can be distinctly enhanced again with thinner samples and an optimized heat-transfer behavior. This means that infrared crosslinking is already distinctly below the manufacturer-specified vulcanization times of more than 15 minutes. In this connection, the printing bed can have the intended shape of the implant (see FIG. 4) or a straight shape, and in this case the intended 3D structure must be projected onto the 2D plane of the printing bed. Subsequently, in the next step, the conductor material (e.g., silver conductive paste) can be applied using a second dispenser to the base shape generated. Afterwards, in the last step of the method, silicone rubber is sprayed and crosslinked, and so the conductor material is completely encapsulated in silicone. Alternatively, the implant can be produced in a lowerable prepolymer bath by layer-by-layer in situ vulcanization. Occasionally, what is crucial for the shape accuracy and the resolution of the method is the distinct demarcation of the vulcanized material from the prepolymer. To this end, the diameter of the laser beam should be matched to the size of the target structures. Since the silicone rubber already crosslinks at room temperature, the production process should be carried out quickly in order to achieve a strict discrimination between prepolymer and component. Alternatively, in the case of crosslinking in a polymer bath, it is possible to use, instead of a high-performance laser, multiple weaker lasers having the same focal point but different beam paths, and so primarily only the volume to be crosslinked and not the edge regions are irradiated.

Figure 5:
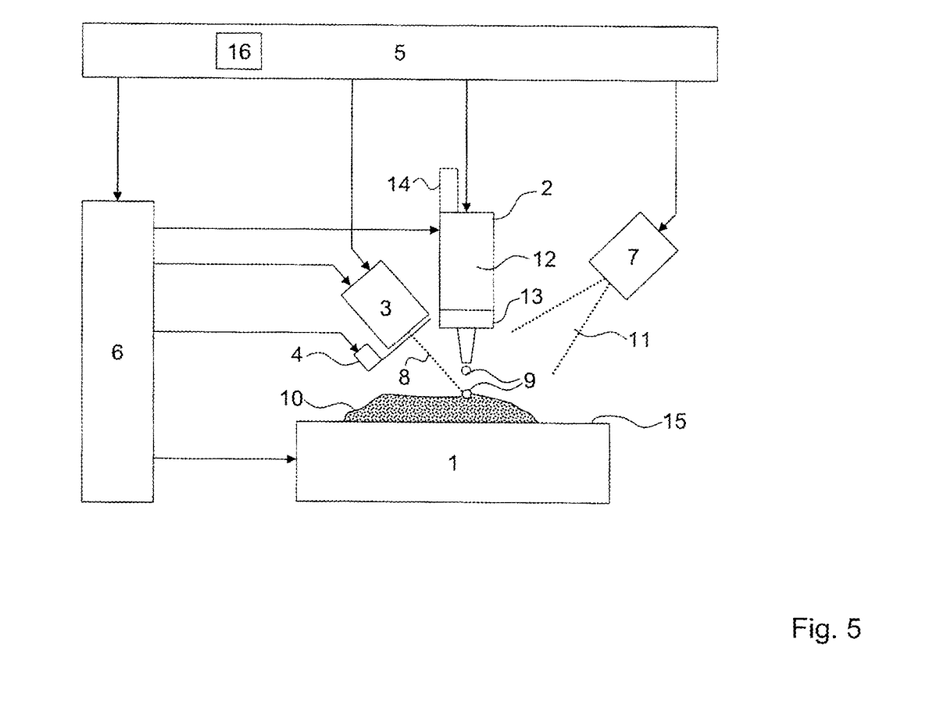
FIG. 5—A schematic depiction of an apparatus for producing a component by means of an additive manufacturing process.

The apparatus depicted in highly schematic form in FIG. 5 for the production of a component 10 comprises the following components: a manufacturing zone 1 having a platform 15, a raw material dispensing unit 2, a light-beam source 3, a shutter 4, a control unit 5 with a computer 16, an actuator mechanism 6 and a heat source 7. For example, the component 10 is produced in the manufacturing zone 1 on the platform 15 by means of the additive manufacturing process. To this end, the raw material dispensing unit 2 dispenses, from raw material 12 kept available in liquid form therein, raw material drops 9. After they impact in the manufacturing zone 1, the raw material drops 9 are heated and thus solidified by a light beam 8 of the light-beam source 3. To carry out the additive manufacturing process, it is necessary to alter the position of the raw material dispensing unit relative to the manufacturing zone 1 or to the component 10 already produced in part thereon. In this case, the light-beam source 3 must be repositioned to the same extent. The actuator mechanism 6 serves for this purpose. For example, said mechanism can be designed such that the manufacturing zone 1 is, for example, moved in two directions in space in a horizontal plane. In addition, a possibility for adjustment in the third direction in space, i.e., upward and downward, can also be present. Alternatively or additionally, the actuator mechanism 6 can also alter the light-beam source 3 and the raw material dispensing unit 2 with respect to their position.

The control unit 5 controls the entire manufacturing process such that the individual method steps are controlled by a computer 16 on which a computer program runs, for example by the raw material dispensing unit 2 for dispensing a raw material drop 9 being controlled and the actuator mechanism 6 for the appropriate positioning of the individual components being controlled. Moreover, it is possible, via the control unit 5, to control the light-beam source 3 with respect to the light emission of the light beam 8, for example by switching-on and switching-off of the light beam 8. If a light-beam source 3 is used in which the switching-on and switching-off of the light beam 8 cannot be done within the necessary short time, the shutter 4 can be additionally used. Said shutter acts as a screen introducible into the light beam 8, and so, by mechanical actuation of the shutter 4, for example from the actuator mechanism 6, the light beam 8 of the light-beam source 3 can be interrupted for a short time and be uninterrupted again.

The raw material dispensing unit 2 can comprise a preheating unit 13 by means of which the liquid raw material 12 can be already preheated and thus partially solidified in the raw material dispensing unit 2. Furthermore, the raw material dispensing unit 2 can comprise a reserve of curing-promoting and/or electrically conductive material 14 which can be admixed with the raw material 12 via a mixer. In this way, it is possible, for example, to admix carbon nanotubes for the production of conductive regions of the component 10 with the raw material 12 as required.

The heat source 7 is intended for achieving a conclusive complete curing of the raw material. Said curing can likewise be controlled via the control unit 5, for example be switched on and switched off. By means of the heat source 7, heat radiation 11 is radiated onto the component 10, making it possible to achieve a heat after-treatment of the component 10.

Figure 6:
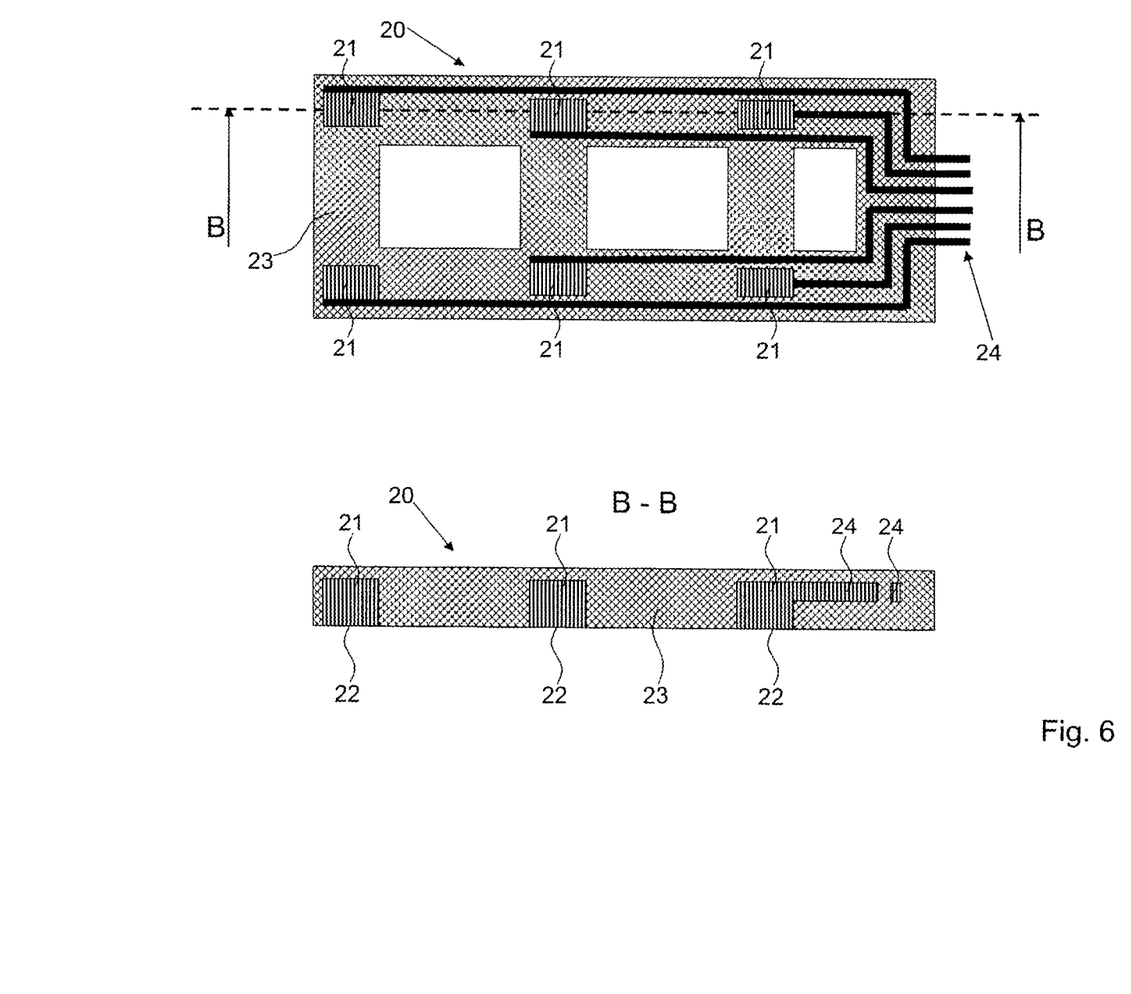
FIG. 6—A personalized grid electrode array 20.

FIG. 6 shows the medical implant in the form of the grid electrode array 20 additionally in a sectional view from the top and in a cross-sectional view in the section plane B-B (bottom part of FIG. 6). In this case, it is possible to discern six electrodes 21 which are electrically contacted via connecting lines 24. The connecting lines 24 are guided out of the rubbery-elastic material 23 of the implant at a connection side. Furthermore, it is possible to discern that a particular external contact surface 22 of the electrodes 21 is not covered by the rubbery-elastic material 23, ensuring a good electrical contacting in relation to the tissue surface of the patient.

The invention claimed is:

1. A method for producing a component by an additive manufacturing process, wherein the component is entirely or partly produced from a liquid raw material solidifiable by heating, the method comprising
    preheating, by a preheating unit, the liquid raw material in a raw material dispensing unit such that the liquid raw material is partially solidified,
    dispensing the partially solidified raw material into a manufacturing zone, and
    heating and thereby solidifying the raw material by computer-controlled, punctual targeted light irradiation, wherein the impact point of a light beam of a light-beam source relative to the manufacturing zone is moved continuously and/or in a stepwise manner.

2. The method as claimed in claim 1, wherein the raw material is a polymer material.

3. The method as claimed in claim 1, further comprising repositioning the impact point of the light beam of the light-beam source relative to the manufacturing zone during the manufacturing process for the component, wherein the impact point of the light beam is repositioned in relation to a raw material dispensing unit which dispenses the raw material in a dropwise manner such that raw material drops freshly dispensed by the raw material dispensing unit are immediately heated and thereby solidified by the light beam.

4. The method as claimed in claim 1, further comprising mixing the raw material with a curing-promoting material.

5. The method as claimed in claim 1, wherein the light beam is an infrared light beam or has at least predominantly infrared spectral components.

6. The method as claimed in claim 1, further comprising producing the component from multiple different materials, with at least one holding structure for at least one subelement of the component being generated from the raw material solidified by light irradiation.

7. The method as claimed in claim 1, wherein the raw material is not completely solidified by means of the computer-controlled, punctual targeted light irradiation in a first pass.

8. The method as claimed in claim 1, further comprising applying one or more liquid raw material points to one or more of a platform and already solidified raw material, and solidifying the one or more liquid raw material points by light irradiation before further points of liquid raw material are applied.

9. The method as claimed in claim 1, further comprising applying the liquid raw material in a layer-by-layer manner to one or more of a platform and already solidified raw material, and solidifying the applied liquid raw material by computer-controlled, targeted light irradiation before a further layer of liquid raw material is applied.

10. The method as claimed in claim 1, further comprising subjecting the component to a heat after-treatment after complete or partial conclusion of the heating and solidification step for the liquid raw material by computer-controlled, targeted light irradiation.

\* \* \* \* \*